(12) United States Patent
Coates et al.

(10) Patent No.: US 7,815,620 B2
(45) Date of Patent: Oct. 19, 2010

(54) PROTECTIVE ABSORBENT ARTICLE WITH ATTACHED ADJUSTABLE BELT WITH BUTTON FASTENERS

(76) Inventors: Fredrica V. Coates, 400 Stanton Ct., Winston-Salem, NC (US) 27106; Donald A. Sheldon, 513 Larkin's Bridge Dr., Downingtown, PA (US) 19335

( * ) Notice: Subject to any disclaimer, the term of this patent is extended or adjusted under 35 U.S.C. 154(b) by 690 days.

(21) Appl. No.: 10/484,279

(22) PCT Filed: Jul. 25, 2002

(86) PCT No.: PCT/US02/23591
§ 371 (c)(1),
(2), (4) Date: Jun. 9, 2004

(87) PCT Pub. No.: WO03/009794

PCT Pub. Date: Feb. 6, 2003

(65) Prior Publication Data
US 2004/0236304 A1 Nov. 25, 2004

Related U.S. Application Data

(60) Provisional application No. 60/307,383, filed on Jul. 25, 2001, provisional application No. 60/307,381, filed on Jul. 25, 2001, provisional application No. 60/307,382, filed on Jul. 25, 2001.

(51) Int. Cl.
*A61F 13/15* (2006.01)

(52) U.S. Cl. ................. 604/392; 604/393; 604/389; 604/402; 604/386; 604/387; 604/390; 604/396

(58) Field of Classification Search ......... 604/392–399, 604/402, 386–387, 179, 390; 2/319, 265, 2/309; 128/100.1, 100; 24/89, 93
See application file for complete search history.

(56) References Cited

U.S. PATENT DOCUMENTS 786,136 A * 3/1905 Haller ................. 604/398
1,206,167 A * 11/1916 Swetzel .............. 604/392

(Continued)

FOREIGN PATENT DOCUMENTS

CH 252647 1/1948

(Continued)

OTHER PUBLICATIONS

International Search Report, Application No. PCT/US02/23591, dated Aug. 11, 2003.

*Primary Examiner*—Jacqueline F. Stephens
(74) *Attorney, Agent, or Firm*—Adams Intellectual Property Law

(57) ABSTRACT

An adjustable absorbent article is provided according to exemplary aspects of this invention. The absorbent article includes a body portion configured to be positioned adjacent a wearer of the absorbent article. The absorbent article includes at least one belt having end portions, at least one of which end portions is configured to be engaged to the body portion. A first means is positioned on at least one of the end portions of the belt for releasable engagement of the end portion to the body portion, and a second means is positioned at a location spaced from the end portions of the belt for releasable engagement to the belt or the body portion to adjust the length of the belt.

30 Claims, 8 Drawing Sheets

U.S. PATENT DOCUMENTS

| | | | | |
|---|---|---|---|---|
| 1,329,119 | A * | 1/1920 | George | 604/394 |
| 1,669,188 | A * | 5/1928 | Condylis | 604/386 |
| 1,800,739 | A * | 4/1931 | Marinsky | 604/402 |
| RE20,315 | E * | 3/1937 | Lesueur | 604/394 |
| 2,545,761 | A * | 3/1951 | Brink | 604/394 |
| 2,568,910 | A * | 9/1951 | Condylis | 604/392 |
| 2,711,736 | A * | 6/1955 | Petitpas | 604/397 |
| 3,324,856 | A * | 6/1967 | Young | 604/394 |
| 3,788,323 | A * | 1/1974 | Robinson | 604/399 |
| 4,114,621 | A * | 9/1978 | Mims, Jr. | 604/361 |
| 4,315,508 | A * | 2/1982 | Bolick | 604/371 |
| 4,728,326 | A | 3/1988 | Gilles | |
| 4,886,512 | A | 12/1989 | Damico et al. | |
| 4,920,581 | A * | 5/1990 | Gray | 2/237 |
| 5,368,585 | A | 11/1994 | Dokken | |
| 5,374,262 | A | 12/1994 | Keuhn et al. | |
| H1440 | H * | 5/1995 | New et al. | 604/386 |
| 5,624,428 | A | 4/1997 | Sauer | |
| 5,704,933 | A * | 1/1998 | Fell et al. | 604/399 |

FOREIGN PATENT DOCUMENTS

| | | |
|---|---|---|
| CH | 298320 | 4/1954 |
| EP | 0 605 013 A1 | 7/1994 |
| FR | 602512 | 3/1926 |
| FR | 652924 A | 3/1929 |
| FR | 669468 A | 11/1929 |
| FR | 1030901 | 6/1953 |
| FR | 1117156 | 5/1956 |
| FR | 1294232 | 5/1962 |
| WO | WO 97/31605 | 9/1997 |
| WO | WO 98/48750 | 11/1998 |
| WO | WO 9848750 A1 * | 11/1998 |
| WO | WO 03/009794 A2 * | 2/2003 |

* cited by examiner

PROTECTIVE ABSORBENT ARTICLE WITH ATTACHED ADJUSTABLE BELT WITH BUTTON FASTENERS

CROSS REFERENCE TO RELATED APPLICATIONS

This is a U.S. National Phase of International Application No. PCT/US02/23591 filed Jul. 25, 2002.

This application claims priority of U.S. Provisional Patent Application No. 60/307,383 by Fredrica Coates, filed Jul. 25, 2001, titled STATIONARY BUTTON STRAP FOR SECURE FIT OF BELTED UNDERGARMENT; U.S. Provisional Patent Application No. 60/307,381 by Fredrica Coates, filed Jul. 25, 2001, titled BUTTONHOLE ELASTIC IN COMBINATION WITH UNDERGARMENT; and U.S. Provisional Patent Application No. 60/307,382 by Fredrica Coates, filed Jul. 25, 2001, titled BELTED UNDERGARMENT WITH STATIONARY BUTTONED BELT AND CUFF, each of which is incorporated herein by reference.

FIELD OF THE INVENTION

This invention relates to protective undergarments. More specifically, it relates to belts for protective undergarments configured for adjustability and ease of use.

BACKGROUND OF THE INVENTION

The use of absorbent articles, such as protective undergarments, has increased steadily for many years. Early uses, such as diapers for babies and sanitary products for women, have in recent years been joined by an increasing demand for products designed to deal with incontinence issues for adults, frequently brought on by advanced age, obesity, or a variety of medical conditions. At the same time, markets have grown in all of these areas for both disposable and reusable products, depending on the preferences of the consumer.

Disposable absorbent articles, such as diapers and pads for example, are in widespread use throughout the world as a result of their convenience. They provide substantial advantages and convenience over absorbent articles that have to be laundered and reused, particularly when the absorbent articles are used away from home. In recent years, many different disposable absorbent articles have been proposed and some have been very successful in the marketplace. However, even current successful products leave room for improvement.

To promote preservation of the environment, some consumers desire to return to the use of reusable, rather than disposable, absorbent articles such as infant and adult diapers. A recent improvement to reusable diapers is in the replacement of pin fasteners by fasteners of filamentary material, such as hook and loop filamentary materials manufactured by Velcro Corporation and Aplix Corporation. In this regard, reference is made to U.S. Pat. No. 4,537,591 to Coates, incorporated herein by reference, which discloses a cloth diaper having filamentary fasteners together with a self-closing tab cover that protects the fasteners from buildup of lint during washing.

Whether for reusable or disposable products, various fastening systems have been employed for fastening the absorbent products to the wearer or to the clothing of the wearer. For example, the waistband of a diaper is preferably fastened around the waist of the wearer, and the fastening system is generally intended to hold the diaper in snug encircling fashion on the wearer's torso.

The manipulation of reusable and/or disposable products for adults, especially the infirm or obese, and/or those with limited dexterity, is sometimes made difficult by the size and weight of the person wearing the garment. These factors hinder the donning and doffing of protective undergarments having traditional configurations. Also, traditional configurations are not easily adjustable to fit the waistlines of various wearers. Thus there continues to be a need for undergarments with improved adjustability and ease of use.

SUMMARY OF THE INVENTION

An adjustable absorbent article is provided according to exemplary aspects of this invention. The absorbent article includes a body portion configured to be positioned adjacent a wearer of the absorbent article. The absorbent article includes at least one belt having end portions, at least one of which end portions is configured to be engaged to the body portion. A first means is positioned on at least one of the end portions of the belt for releasable engagement of the end portion to the body portion, and a second means is positioned at a location spaced from the end portions of the belt for releasable engagement to the belt or the body portion to adjust the length of the belt.

According to another exemplary aspect of this invention, an adjustable absorbent article is provided. The absorbent article includes a body portion. The absorbent article also includes at least one belt having end portions configured to be attached to the body portion and to retain the body portion adjacent a wearer of the absorbent article. At least one end portion of the belt has a button or a buttonhole for engagement with a buttonhole or button respectively on the body portion. The belt has at least one buttonhole spaced from the end portions of the belt for engagement with a button to adjust the size of the belt.

According to another exemplary aspect of this invention, an adjustable absorbent article is provided, including a body portion and belts. Each of the belts has end portions configured to be attached to the body portion and to retain the body portion adjacent a wearer of the absorbent article. At least one end portion of each of the belts has a button for engagement with a buttonhole on the body portion. Each of the belts has a plurality of buttonholes spaced from the end portions of the belts for optional selective engagement with the button to adjust the size of each of the belts.

According to still another exemplary aspect of this invention, a belt extender is configured to be attached to a body portion and a belt of an absorbent article for adjusting the size of the absorbent article. End portions of the belt extender each has a button or a buttonhole for engagement with a buttonhole or button respectively on the body portion or belt of the absorbent article. The belt extender has at least one buttonhole spaced from the end portions for engagement with a button of the absorbent article to adjust the fit of the absorbent article.

According to yet another exemplary aspect of this invention, an adjustable absorbent article is provided. The absorbent article includes a body portion. The absorbent article also includes a belt attached to the body portion to help retain the body portion adjacent a wearer of the absorbent article. The belt has at least one button and at least one buttonhole. The buttonhole is positioned for engagement of the button, thereby reducing the size of the belt.

Another exemplary aspect of this invention provides a belt configured to be attached to a body portion of an absorbent article to retain the body portion adjacent a wearer of the absorbent article and for adjusting the size of the absorbent article. End portions of the belt each has a button for engagement with a respective buttonhole on the body portion of the absorbent article. The belt has at least one buttonhole spaced from the end portions for engagement with at least one of the buttons of the belt or a button on the absorbent article to adjust the size of the absorbent article.

BRIEF DESCRIPTION OF DRAWINGS

The invention is best understood from the following detailed description when read in connection with the accompanying drawings. It is emphasized that, according to common practice, the various features of the drawings are not rendered to any particular proportion or scale. On the contrary, the dimensions of the various features are arbitrarily expanded or reduced for clarity. Included in the drawings are the following figures.

DETAILED DESCRIPTION OF THE INVENTION

Exemplary features of selected embodiments of this invention will now be described with reference to the figures. It will be appreciated that the spirit and scope of the invention is not limited to the embodiments selected for illustration. It is contemplated that any of the configurations and materials described hereafter can be modified within the scope of this invention.

Referring to the figures generally, an adjustable absorbent article is provided according to exemplary aspects of this invention. The absorbent article includes a body portion configured to be positioned adjacent a wearer of the absorbent article. The absorbent article includes at least one belt having end portions, at least one of which end portions is configured to be engaged to the body portion. A first means is positioned on at least one of the end portions of the belt for releasable engagement of the end portion to the body portion, and a second means is positioned at a location spaced from the end portions of the belt for releasable engagement to the belt or the body portion to adjust the length of the belt.

The adjustable absorbent article optionally includes two or more belts each having end portions, first means positioned on at least one of the end portions of each of the belts for releasable engagement of the end portion to the body portion, and second means positioned at a location spaced from the end portions of each of the belts for releasable engagement to the belts or the body portion to adjust the length of the belts. The first releasable engagement means is optionally positioned on each of the end portions of each of one or more belts, and each of the end portions of a particular belt can be configured to be engaged to the body portion of the absorbent article.

The first and second releasable engagement means may be provided in the form of a button, a buttonhole, hooks, a surface configured to engage hooks, an adhesive, or any other engagement mechanism known in the art. The first and second releasable engagement means are optionally engageable to one another, and the second releasable engagement means can be positioned at plural locations spaced from the end portions of the belt.

The second releasable engagement means is optionally positioned for releasable engagement to the belt to adjust the length of the belt. Alternatively, the second releasable engagement means may be positioned for releasable engagement to the body portion of the absorbent undergarment to adjust the length of the belt.

Figure 1:
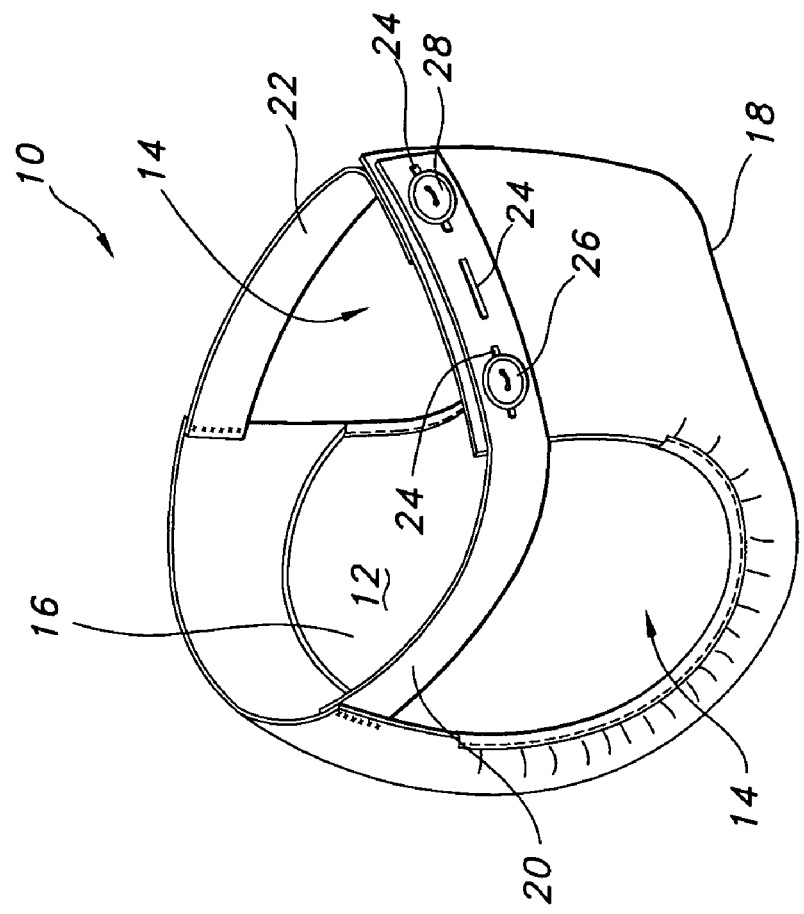
FIG. 1 is a perspective view of an exemplary embodiment of an undergarment according to aspects of this invention.

Referring to the embodiment illustrated in FIG. 1, an adjustable absorbent article such as the protective undergarment 10 is provided according to aspects of this invention. The undergarment 10 includes a body portion such as undergarment body 12. The undergarment 10 also includes at least one belt, such as belts 20 and 22 for example, having end portions configured to be attached to the body portion 12 and to retain the body portion 12 adjacent a wearer of the absorbent article. As used herein, the term "belt" refers to a segment that, alone or in combination with the undergarment body and/or one or more other belts, helps to retain a garment to the body of a wearer. At least one end portion of the belt has a button, such as button 28, or a buttonhole, such as buttonholes 24, for engagement with a buttonhole or button respectively on the body portion. The belt has at least one buttonhole spaced from the end portions of the belt for engagement with a button to adjust the size of the belt.

In the exemplary embodiment of FIG. 1, button 28 is on belt 22 and buttonholes 24 are on belt 20. The undergarment is secured by pushing button 26, on front section 18, through one of buttonholes 24 of belt 20, and then pushing button 28, on belt 22, through a buttonhole (hidden from view) in front section 18 and then through another of buttonholes 24 of belt 20. Accordingly, the front section 18 is positioned between the user's body and the belt 20 at the location of button 26 and between the belts 20 and 22 at the location of button 28. Front section 18 comprises an absorbent material, which may be disposable or reusable.

The adjustable absorbent article may include only reusable components, only disposable components, or a combination of these. In other words, the adjustable absorbent article may be intended for one-time usage. For example, once the article is soiled or it is no longer needed, it is discarded by the user. Alternatively, the adjustable absorbent article is optionally reusable, depending on preferences of the user and manufacturer. More specifically, the article can be adapted for more than one usage. For example, once the article is soiled, it can be washed for reuse.

The body portion of the absorbent article optionally includes at least one buttonhole, and the belt includes at least one button positioned for engagement in the buttonhole. Alternatively, the body portion optionally includes at least two buttonholes and the belt includes a button at each of the end portions, each of the buttons being positioned for engagement in one of the buttonholes.

In another configuration, the body portion of the adjustable absorbent article optionally includes at least one button and the belt includes at least one buttonhole positioned to engage the button. The body portion can include at least two buttons and the belt can include a buttonhole at each of its end portions, wherein each of the buttonholes is positioned to engage one of the buttons.

In yet another configuration, the body portion of the adjustable absorbent article includes at least one button and at least one buttonhole and the belt includes at least one buttonhole positioned to engage the button and at least one button positioned to be engaged in the buttonhole. The belt optionally includes a plurality of buttonholes between the end portions of the belt, and the buttonholes may or may not be substantially evenly spaced.

Additionally, the belt may also include indicia to assist the wearer in sizing the adjustable absorbent article. The indicia can be numerals, colors, textures, shades, dimensions or any other suitable indicator of size.

Figure 2:
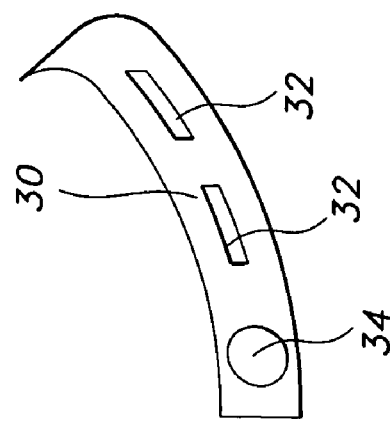
FIG. 2 is a perspective view of an exemplary embodiment of a belt extender adapted for use with the undergarment illustrated in FIG. 1.

Referring for example to FIG. 2, a belt extender such as extender 30 is configured to be attached to a body portion 12 and a belt 22 of an absorbent article such as undergarment 10. Although extender 30 is intended for coupling or extending a belt in this particular embodiment, any extender according to this invention may also serve as the belt itself as opposed to a supplement thereto. End portions of the belt extender 30 each has a button 34 or a buttonhole 32 for engagement with a buttonhole or button respectively on the body portion 12 or belt 20, 22 of the absorbent article. The belt extender 30 includes at least one buttonhole 32 spaced from the end portions of the belt extender 30 for engagement with a button of the absorbent article to adjust the fit of the absorbent article.

The belt extender optionally includes at least one button 34 positioned for engagement in a buttonhole 24 of the absorbent article. Or the belt extender may include a button at each of the end portions, wherein each of the buttons is positioned for engagement in a buttonhole of the absorbent article.

Alternatively, the belt extender can include at least one buttonhole positioned to engage a button of the absorbent article. The belt extender optionally includes a buttonhole at each of its end portions, wherein each of the buttonholes is positioned to engage a button of the absorbent article. In yet another configuration, such as that illustrated in FIG. 2 for example, the belt extender 30 includes at least one buttonhole 32 positioned to engage a button of the absorbent article (e.g., positioned to engage the button 28 on the belt 22 of undergarment 10) and at least one button 34 positioned to be engaged by a buttonhole of the absorbent article (e.g., positioned to be engaged by the buttonhole 24 on the belt 20 of undergarment 10).

Referring specifically to the exemplary embodiment illustrated in FIGS. 1 and 2, a belted undergarment is illustrated wherein a resilient strap is used as an extender, if necessary. More specifically, the exemplary belted undergarment uses buttons to secure the undergarment device to the user. Even more specifically, the illustrated undergarment includes a resilient extender with a plurality of buttonholes to fit the undergarment device to a user with a larger waist size. Details of the undergarment illustrated in FIGS. 1 and 2 are described in Application No. 60/307,383, filed Jul. 25, 2001, entitled STATIONARY BUTTON STRAP FOR SECURE FIT OF BELTED UNDERGARMENT, which is incorporated herein by reference.

FIG. 1 is a perspective view of the belted undergarment, and FIG. 2 is a view of the elastic belt extender. The exemplary undergarment is generally indicated at 10. The undergarment body 12 has a pair of leg apertures 14, a rear section 16 and a front section 18. Two belts 20, 22 comprise the belt portion of the device. The belt 20 ends with a number of buttonholes 24.

Located on the front section 18 is a first securing button 26. Located on the end of belt 22 is a second securing button 28. Thus the device 10 may be fitted to the user as seen in FIG. 1.

The belt extender is represented in FIG. 2 at 30. Belt extender 30 is a resilient strap with a plurality of buttonholes 32 and an extender button 34. Button 34 may be attached, if necessary or desired, to any of the buttonholes 24, and then the belt extender 30 is brought around and attached again by buttonholes 32 to the second securing button 28 located on the end of belt 22. Thus the device 10 may be fitted to a user with a larger waist size. Further, the configuration of the device 10 allows the first securing button 26 to be attached first, holding the front section in place. Then the second securing button 28, or the belt extender 30 and second securing button 28, can be fixed.

Additionally, the exemplary embodiment of a belt extender illustrated in FIG. 2 provides an adjustment for a user having a large waist such as a waist larger than about 54". The belt extender 30 makes it possible to adjust the garment 10 for use by wearers of various sizes.

Depending on cost, performance requirements, particular uses, and manufacturing considerations, various materials can be selected for use in absorbent articles according to this invention. U.S. Pat. No. 6,004,893 to Van Tilburg, which is incorporated herein by reference, describes a variety of such materials and associated constructions.

For example, absorbent pads may be provided with a topsheet that is liquid permeable and, when the article is in use, is in close proximity to the skin of the user. If used, the topsheet is preferably compliant, soft feeling and non-irritating to the user's skin. Such topsheets can be made from any of the materials conventional for this type of use. Non-limiting examples of suitable materials that can be used as a topsheet are woven and non-woven polyester, polypropylene, polyethylene, NYLON, and RAYON and formed thermoplastic films. Suitable films are described, for example, in U.S. Pat. No. 4,324,246 to Mullane and Smith and U.S. Pat. No. 4,342,314 to Radel and Thompson, both of which patents are incorporated herein by reference. Formed films may be selected for the topsheet because they are pervious to liquids and yet non-absorbent. Thus, the surface of the formed film, which is in contact with the body, remains substantially dry and is more comfortable to the wearer.

If a topsheet is used, its inner surface may be secured in contacting relation to an absorbent core. This contacting relationship results in liquid penetrating the topsheet faster than if it were not in contact with the absorbent core. The topsheet can be maintained in contact with the absorbent core by applying adhesive, optionally in spaced, limited areas, to an inner surface of the topsheet. Examples of suitable adhesives used for this purpose include the acrylic emulsion E-1833BT manufactured by Rohm and Haas Company of Philadelphia, Pa. and acrylic emulsions manufactured by H. B. Fuller Company of St. Paul, Minn. Also contemplated are thermoplastic hot melt adhesives such as 34-563A, available from National Starch, Inc.

An absorbent pad also optionally includes an absorbent core that is generally compressible, conformable, and non-irritating to the user's skin. It can comprise any material used in the art for such purpose. Examples of suitable materials are layers of tissue (such as wadding), fibrated comminution pulp (e.g., airfelt), cotton, cellulose acetate, and any of these in combination with a superabsorbent polymer.

Crotch portions (i.e. the portions between the front and rear portions) of the undergarments disclosed herein preferably comprise a material that is impervious to liquids and thus prevents bodily fluids and feces from soiling the clothing of the user. Any material used in the art for such purposes can be utilized herein. Suitable materials include embossed or non-embossed polyethylene and polypropylene films and laminated tissue and non-woven materials.

Exemplary materials and constructions for reusable absorbent articles are described in U.S. Pat. No. 5,891,122 and U.S. Pat. No. 6,254,583, both issued to Coates, both of which are incorporated herein by reference. Additional materials and constructions are well known in the art of reusable absorbent articles.

Figure 3:
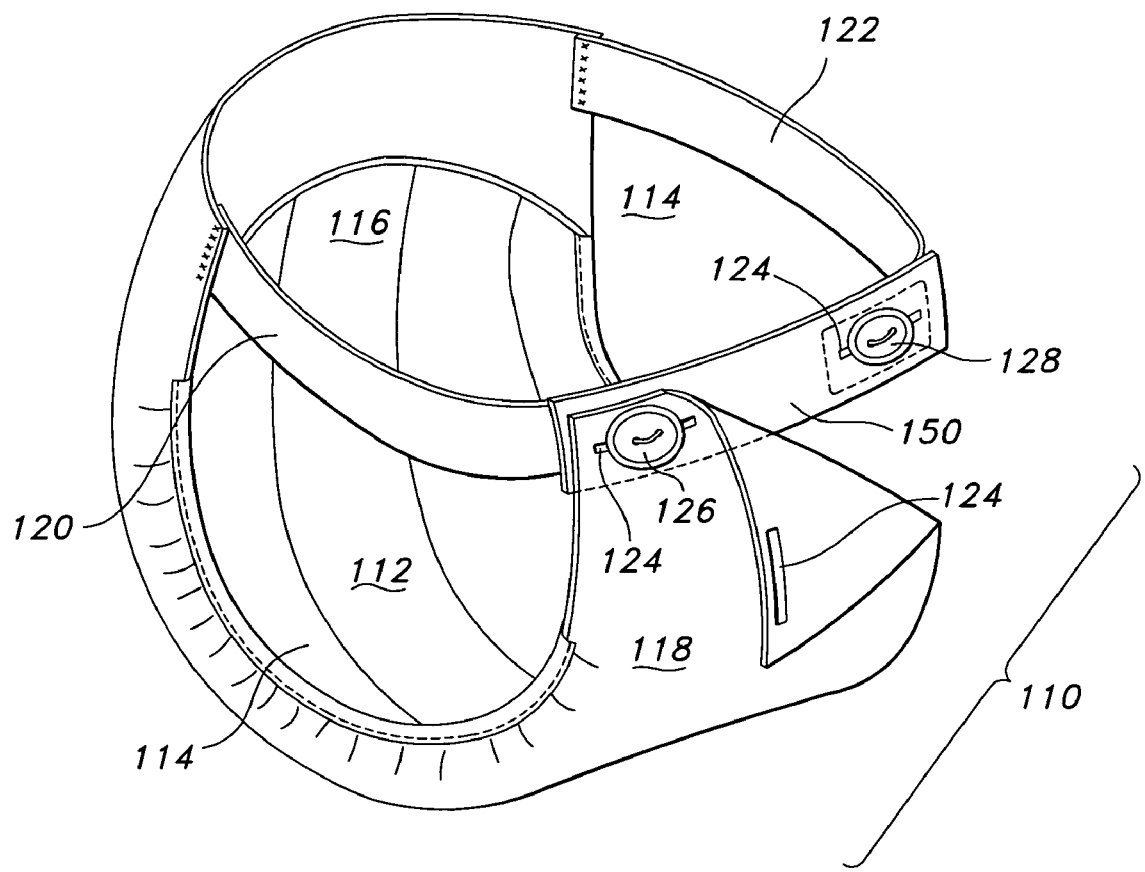
FIG. 3 is a perspective view of another embodiment of an undergarment according to aspects of this invention.
Figure 4:
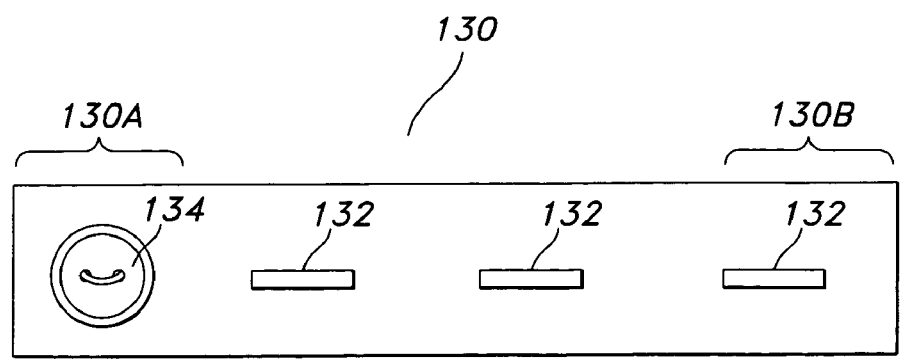
FIG. 4 is a front view of another embodiment of a belt extender configured for use with the undergarment illustrated in FIG. 3.

Referring now to FIGS. 3 and 4, another exemplary embodiment of an undergarment, generally indicated by the numeral 110, is shown. Undergarment 110 is similar to undergarment 10 in that it includes an undergarment body 112, leg apertures 114, a rear section 116, a front section 118, and a pair of belts 120 and 122. In this embodiment, each of the belts 120 and 122 is provided with a button at its end portion. Specifically, belt 120 has a first securing button 126, and belt 122 includes a second securing button 128. A stationary button strap 150 is provided with a pair of buttonholes 124, which are positioned to engage the first securing button 126 of the belt 120 and the second securing button 128 of the belt 122.

The provision of a stationary waist closure, such as that formed by connecting belts 120 and 122 in combination with stationary button strap 150, is advantageous because it eliminates the need for the user to hold the belt stationary with one hand while reaching for the front of the garment with the other hand and then fastening the components to one another. Under such circumstances, the belt or front of the garment may fall out of one's hand, making the garment cumbersome to assemble. The stationary waist closure, such as that illustrated in FIG. 3, holds the waist up while the user completes his or her adjustment of the front. Likewise, in removing the garment, the user has more control.

Thus, in use, the undergarment 110 is assembled by first creating a belt by button-engagement of the stationary button strap 150 to the ends of the belts 120 and 122. The front section 118 of the undergarment 110 can then be engaged to the stationary button strap 150 by engagement of the first and second securing buttons 126 and 128 in the buttonholes 124 that are provided on the front section 118.

Similar to the belt extender 30 discussed above, the embodiment illustrated in FIGS. 3 and 4 includes the optional use of a belt extender 130 having a plurality of buttonholes 132 and an extender button 134. The belt extender 130 can be used to extend the belt formed by the belts 120 and 122 and the stationary button strap 150 of the undergarment 110. More specifically, for example, the second securing button 128 of the belt 122 can be engaged in the buttonhole 132 of the belt extender 130, and the extender button 134 of the belt extender 130 can be engaged in the button hole 124 at the right side of the stationary button strap 150, thereby extending the belt portion of the undergarment 110. The configuration of the belt extender 130 illustrated in FIG. 4 is optionally used for one or both of the belts 120 and 122 of the undergarment 110, thereby providing a belt segment 130, and thereby affording improved adjustability.

Alternatively, when the belt configuration illustrated in FIG. 4 is utilized for belts 120 and 122, the absorbent article 110 is provided with improved adjustability. In other words, an absorbent article like undergarment 110, with or without the optional stationary button strap 150, can include a body portion 112 and belt extenders 130 each having end portions 130A and 130B configured to be attached to the body portion 112 and to retain the body portion 112 adjacent a wearer of the absorbent article. For example, in the embodiment illustrated in FIGS. 3 and 4, one end portion 130A is configured to be attached to the front 118 of the body portion 112 by means of engaging the button 134 on the belt extender 130 into a buttonhole 124 on the body portion 118 (or on stationary button strap 150). The other end portion 130B of the belt extenders 130 can be configured to be attached to the rear 116 of the body portion 112 by means of engaging the buttonhole 132 on the belt extenders 130 with a button on the body portion 112 or by simply attaching the end portion 130B of the belt extender 130 to the rear 116 of the body portion 112 by other means (e.g., sewn as illustrated in FIG. 3, engaged by hook and loop fasteners, or attached in any other manner known in the garment industry). At least one end portion of each of the belt extenders 130 can therefore be provided with a button 134 for engagement with a buttonhole 124 on the body portion 112.

To improve the adjustability of the article, each of the belt extenders 130 can have a plurality of buttonholes 132 spaced from the end portions 130A and 130B of the belt extenders 130 for optional selective engagement with the button 134 to adjust the size of each of the belt extenders 130. More specifically, after button 134 is engaged to a buttonhole 124 on the body 112 of the article, the wearer can optionally select an intermediate buttonhole 132 on one or both belt extenders 130 for engagement to the button 134 (or another button provided on the body portion 112 of the article), thereby doubling the belt over on itself, and thereby shortening the belt to adjust the fit or size of the garment.

Optionally, both end portions of a belt can be provided with a button for engagement with a respective buttonhole on the body portion of the absorbent article. For example, belt extender 130 is optionally provided with a button 134 at end portion 130A (as shown in FIG. 4) and a button at end portion 130B. The belt is also optionally provided with at least one buttonhole, such as one or both of the central buttonholes 132 illustrated in FIG. 4, that is spaced from the end portions of the belt for engagement with at least one of the buttons of the belt or a button on the absorbent article to adjust the size of the absorbent article.

Figure 5:
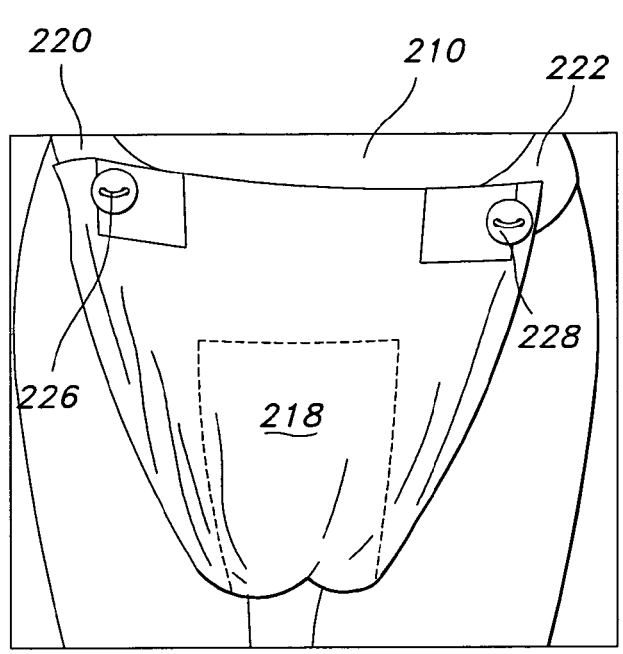
FIG. 5 is a front view of still another embodiment of an undergarment according to aspects of this invention.

Referring now to FIG. 5, another exemplary embodiment of an undergarment, generally designated by the numeral 210, is described. Undergarment 210 includes a pair of belts 220 and 222. The belts 220, 222 terminate at buttons 226 and 228, respectively, which engage a front section 218 of the undergarment 210. Accordingly, the undergarment 210 is similar to the undergarment 110 illustrated in FIG. 3 in that the belts bear the buttons that provide for engagement between the belts and the front section of the undergarment.

Figure 6:
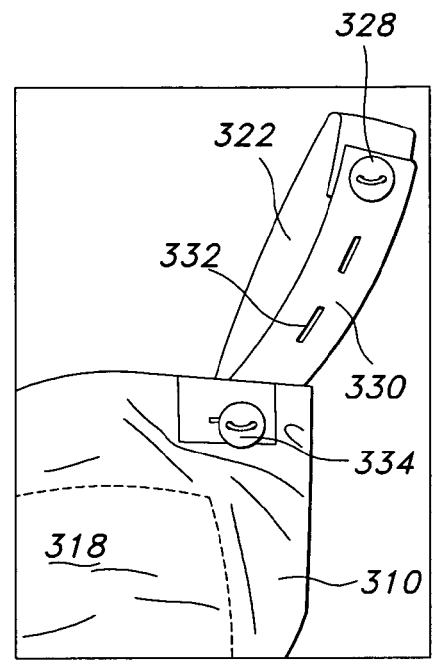
FIG. 6 is a front view of yet another embodiment of an undergarment according to aspects of this invention.

Referring now to FIG. 6, yet another exemplary embodiment of an undergarment, designated by numeral 310, is described. Undergarment 310 is similar to undergarments 210 (FIG. 5) and 110 (FIG. 3) in that it includes a belt 322 and a front section 318. Additionally, undergarment 310 is shown with a belt extender 330 having buttonholes 332 and a button 334. The belt extender 330 extends the belt of the undergarment 310 by providing an extender between the end of the belt 322 and the front section 318. More specifically, a buttonhole 332 on the belt extender 330 engages the button 328 on the belt 322, and the button 334 on the belt extender 330 is engaged by a buttonhole in the front section 318 of the undergarment 310.

Figure 7:
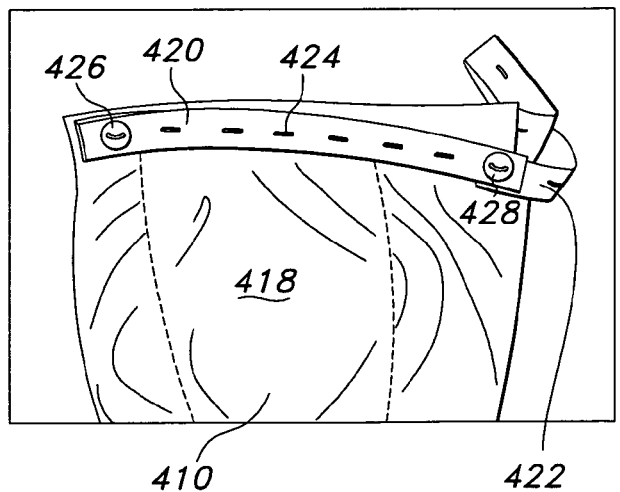
FIG. 7 is a front view of a portion of another embodiment of an undergarment according to aspects of this invention.

Referring now to FIG. 7, another exemplary embodiment of an undergarment according to aspects of this invention is illustrated. The undergarment 410 is similar to the undergarment 10 illustrated in FIG. 1 in that undergarment 410 includes a belt 420 with a series of buttonholes 424. The belt 422 of undergarment 410 includes buttonholes 424 as well as a button 428 for engagement with a buttonhole 424 of the belt 420.

By virtue of the provision of multiple buttonholes 424 on the belt 420 and belt 422 of the undergarment 410, the undergarment 410 is adjustable because the button 428 of the belt 422 can be engaged in any one of a variety of buttonholes 424 and the button 426 can be engaged in any one of the buttonholes 424 of the belt 420.

Figure 8:
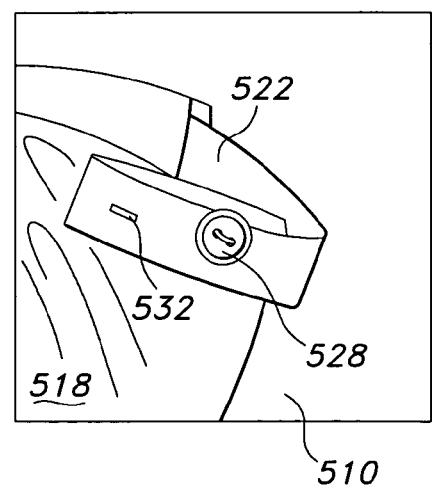
FIG. 8 is a front view of a portion of yet another embodiment of an undergarment according to aspects of this invention.

Referring now to FIG. 8, another exemplary embodiment of an undergarment 510 is illustrated. Undergarment 510 includes a belt 522 including a plurality of buttonholes 532 positioned to engage the button 528 of the front section 518 of the undergarment 510. As illustrated in FIG. 8, the belt 522 is shortened by folding the belt 522 over and inserting the button 528 through a buttonhole 532 provided along the length of the belt 522. By doubling-over the belt 522 in this manner, the belt 522 can be shortened so that the undergarment 510 can be adjusted in size in order to fit a particular wearer. Although not shown in FIG. 8, it will be understood that a similar configuration can be used on the opposite belt of the undergarment 510 (not shown).

It will be appreciated that engagement mechanisms other than buttons and buttonholes can be employed to assemble an undergarment according to this invention. Although buttons and buttonholes are employed in the exemplary embodiments illustrated in FIGS. 1-8, other mechanisms can certainly be used depending upon the preferences of the user and/or manufacturer of the undergarment. Cost considerations and ease of use are additional factors.

Figure 9:
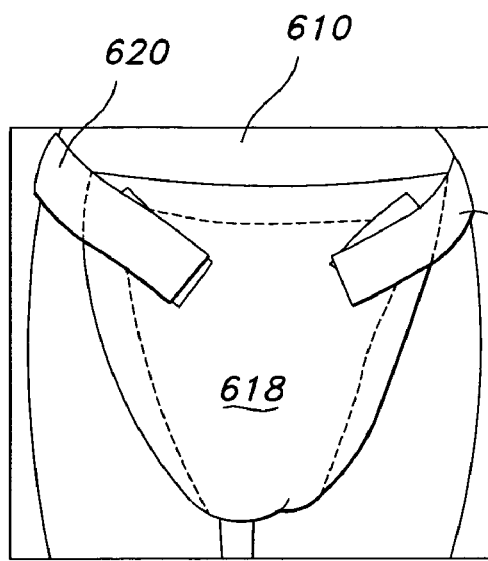
FIG. 9 is a front view of another embodiment of an undergarment according to aspects of this invention.

For example, referring to FIGS. 9-12, hook and loop fasteners are optionally employed. Referring to FIG. 9, for example, an exemplary undergarment 610 includes a pair of belts 620 and 622 that engage a front section 618 of the undergarment 610 by means of hook and loop fasteners such as those available from the Velcro Corporation under the mark VELCRO. The embodiment of undergarment 610 illustrated in FIG. 9 is similar to that illustrated in FIG. 5 except that hook and loop fasteners replace the button/buttonhole mechanism.

Figure 10:
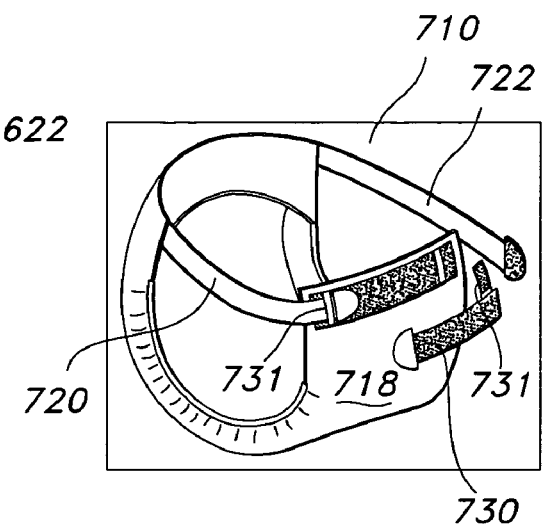
FIG. 10 is a perspective view of still another embodiment of an undergarment according to aspects of this invention.

Referring to FIG. 10, an exemplary undergarment 710 includes belts 720 and 722 as well as a belt extender 730, each of which employs the hook and loop fastener engagement mechanism. Undergarment 710 also employs securing flaps 731 in order to help ensure an adequate engagement between each of the belts 720 and 722 and the front section 718 of the undergarment 710. The securing flaps 731 can simply be formed by a strip of material that is positionable over the end portion of the belt 720 or 722 in order to supplement the engagement between the hook and loop fasteners provided on the belts 720 and 722 and the front section 718 of the undergarment 710. The shape or contour provided at the end of each of the belts 720 and 722 also helps to prevent or resist unintended retraction of the belts 720 and 722 from within the securing flaps 731.

Figure 11:
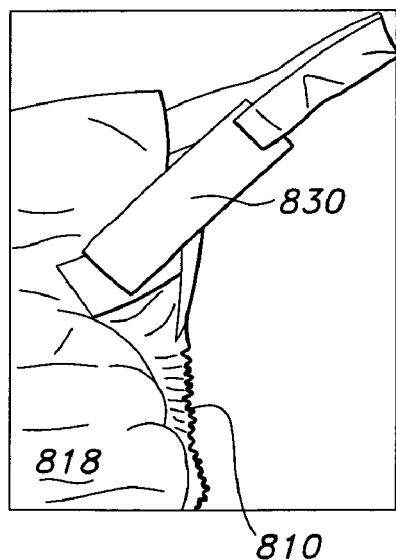
FIG. 11 is a front view of a portion of yet another embodiment of an undergarment according to aspects of this invention.

Referring now to FIG. 11, an exemplary embodiment of an undergarment 810 includes a belt extender 830 to provide an elongating connection between the belt 822 of the undergarment 810 and the front section 818 of the undergarment 810. Because the engagement between the belt 822 and the belt extender 830 can be positioned according to the user's preference, the belt portion of the undergarment 810 can be adjusted to fit a variety of waist sizes. Similarly, the point of engagement between the belt extender 830 and the front section 818 of the undergarment 810 can be selected so as to provide some adjustability as well.

Figure 12:
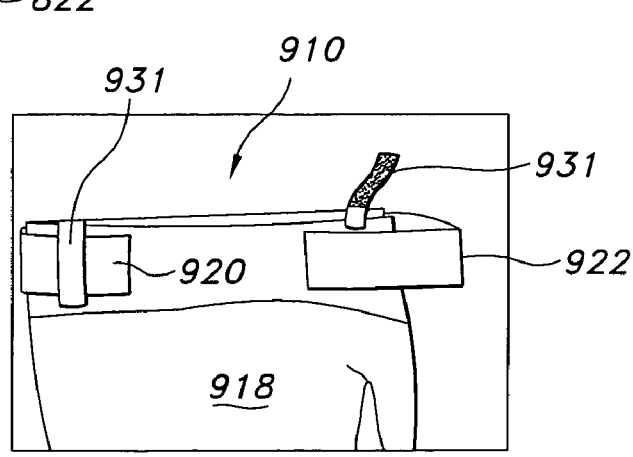
FIG. 12 is a front view of a portion of still another embodiment of an undergarment according to aspects of this invention.

Referring now to FIG. 12, an exemplary embodiment of an undergarment 910 is illustrated with a belt 920 and a belt 922 both engaged to a front end 918 of the undergarment 910. A pair of securing flaps 931 are provided (one shown in an engaged position and the other shown in a disengaged position). The securing flaps 931 help to retain the end portions of the belts 920 and 922 in engagement with the front end 918 of the undergarment 910.

Accordingly, a resilient belt extender with double-sided hook and loop closures at each end can be provided for attachment to a belt product for accommodating users with larger waist sizes such as those having a waist size larger than about 42". Additionally, a double-sided hook and loop fastener can be provided at the end of a belt such that the belts can actually overlap and attach to each other making the waist smaller for fragile and petite torsos. The securing flaps (or belt-locks) can be provided to help keep the belt from coming loose.

According to another aspect of this invention, an undergarment is provided wherein the size of the waist belt can be changed by overlapping and buttoning the belt to itself. More specifically, referring to FIGS. 13 and 14, an exemplary undergarment can be provided with a resilient waistband that has buttons to allow the user to overlap the elastic portion and button it to itself so that the size of the band can be adjusted to the user's waist size. Details of the undergarment illustrated in FIGS. 13 and 14 are provided in U.S. Application No. 60/307,381, filed Jul. 25, 2001, entitled BUTTONHOLE ELASTIC IN COMBINATION WITH UNDERGARMENT, which is incorporated herein by reference.

Figure 13:
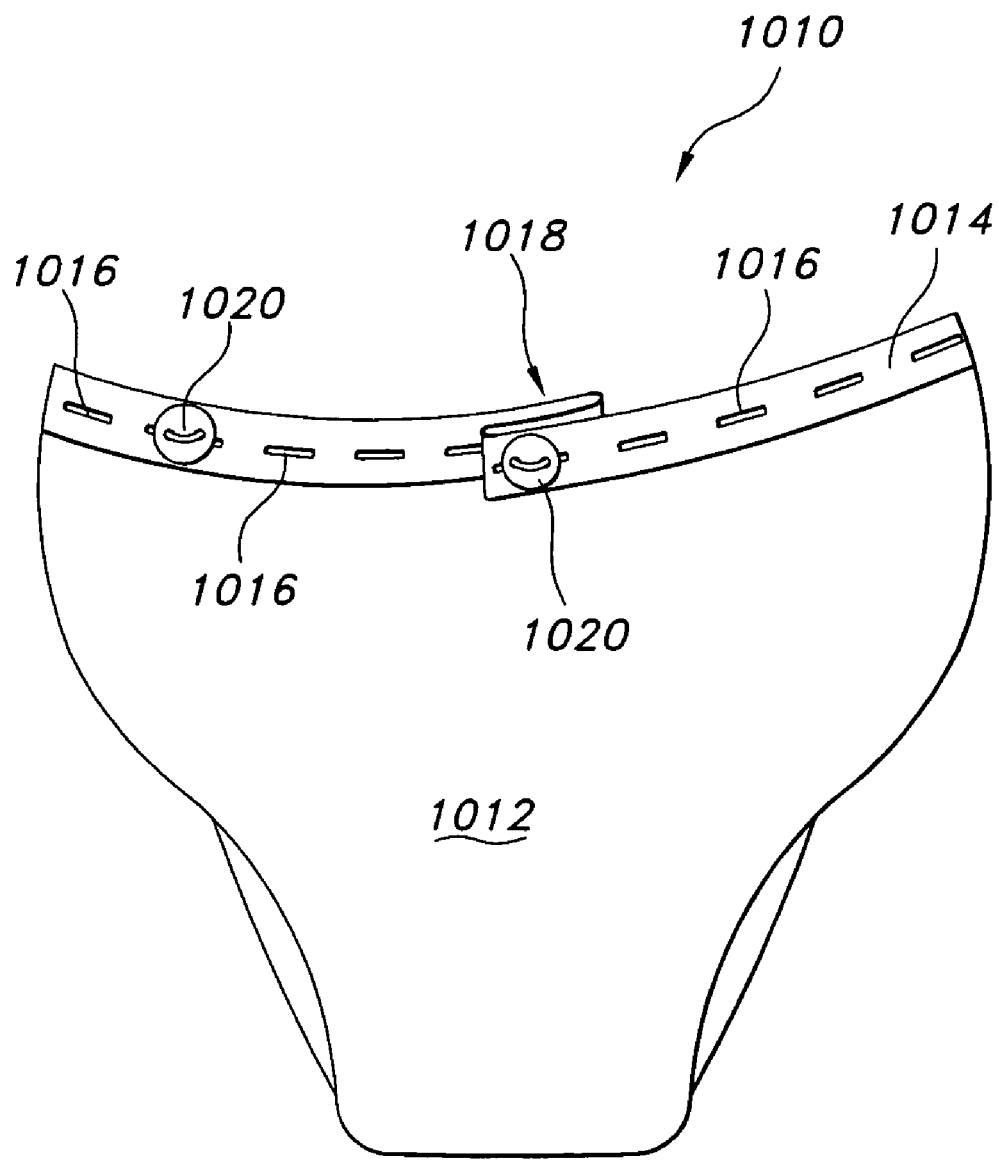
FIG. 13 is a front view of another embodiment of an undergarment according aspects of this invention.
Figure 14:
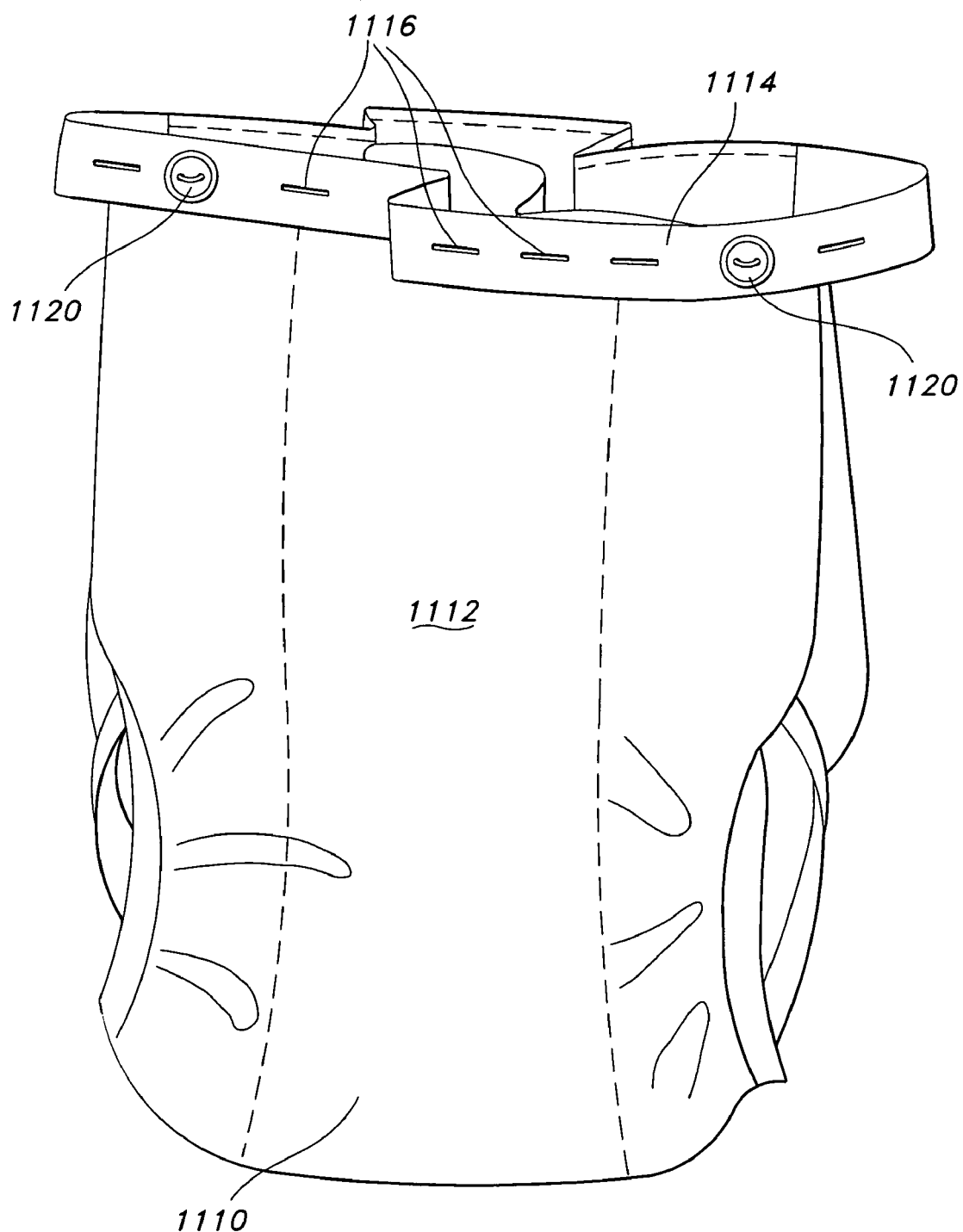
FIG. 14 is a front view of yet another embodiment of an undergarment according to aspects of this invention.

FIG. 13 is a front view of an exemplary undergarment 1010 showing a buttoned elastic waistband partially overlapped. The undergarment 1010 includes a body portion 1012 and a belt, such as a waistband 1014, attached to the body portion 1012 to help is retain the body portion 1012 adjacent a wearer of the absorbent article. The belt 1014 has at least one button 1020 and at least one buttonhole 1016. The buttonhole 1016 is positioned for engagement of the button 1020, thereby reducing the size of the belt 1014, which is optionally overlapped as indicated at 18.

The belt 1014 can include a plurality of buttons 1020 configured for engagement in the at least one buttonhole 1016. Alternatively, the belt 1014 can include a plurality of buttonholes 1016 between an adjacent pair of the buttons 1020. The buttons 1020 provided on the waistband 1014 are fixed and thus the waistband size can be altered to fit the convenience of the user.

In another configuration, the belt 1014 can include a plurality of buttonholes 1016 configured to engage the at least one button 1020. The belt 1014 can also include a plurality of buttonholes 1016 and a plurality of buttons 1020 configured for engagement by one or more of the buttonholes 1016.

Referring now to FIG. 14, the exemplary embodiment of an undergarment 1110 includes a body portion 1112 having a waistband 1114 that, in this particular embodiment, is formed from a resilient material. Waistband 1114 is provided with a series of buttonholes 1116 as well as a plurality of buttons 1120 (two shown in FIG. 14). It will be understood that one or more of the buttons 1120 can be used by the wearer of the undergarment 1110 to engage one or more of the buttonholes 1116 in the waistband 1114, thereby overlapping the waistband 1114 and reducing the size of the waistband 1114. In this manner, the size of the undergarment 1110 can be adjusted to fit the waist of a particular wearer.

Figure 15:
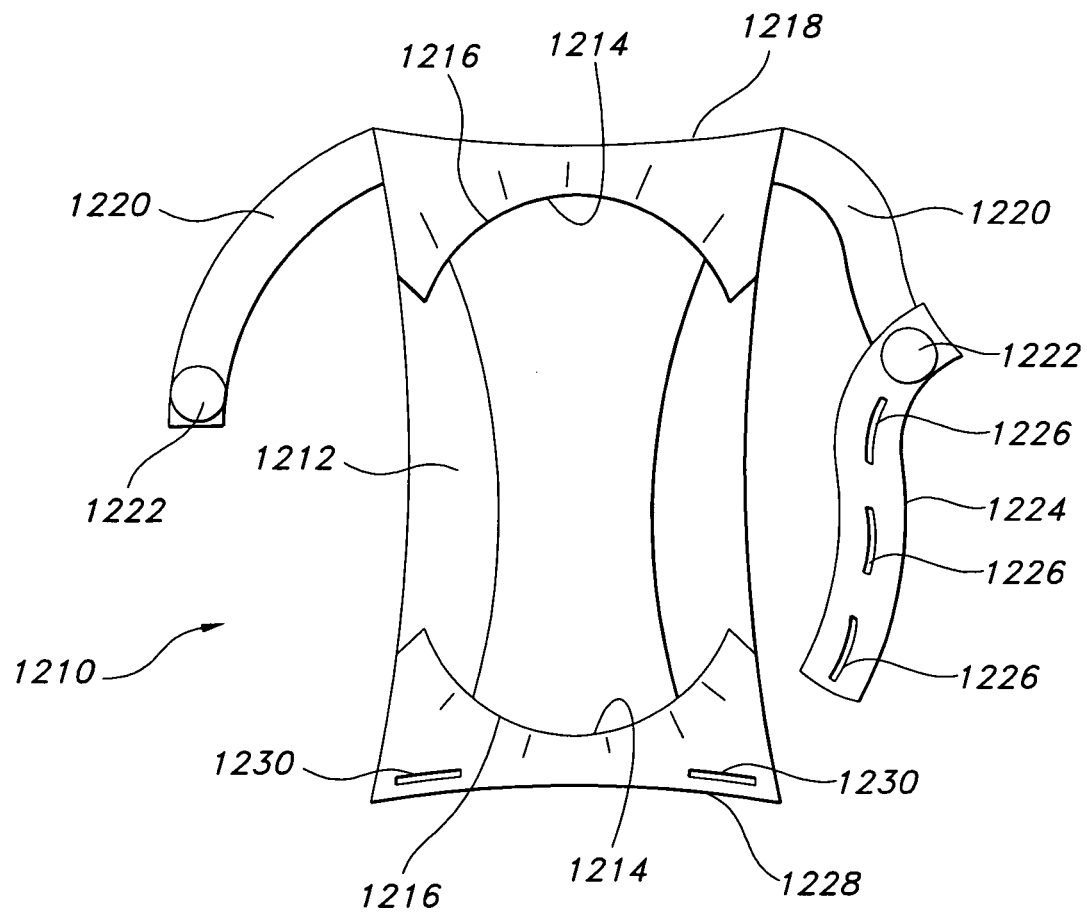
FIG. 15 is a front view of still another embodiment of an undergarment according to aspects of this invention.
Figure 16:
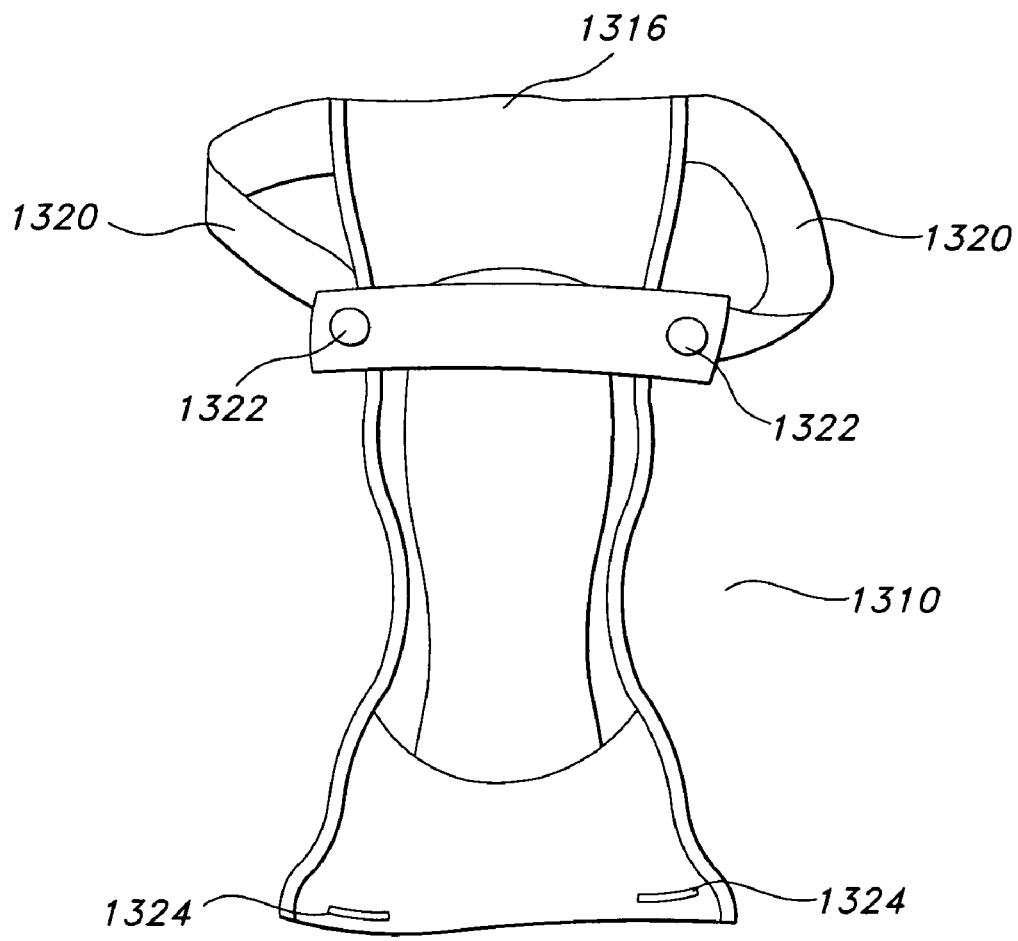
FIG. 16 is a front perspective view of another embodiment of an undergarment according to aspects of this invention.
Figure 17:
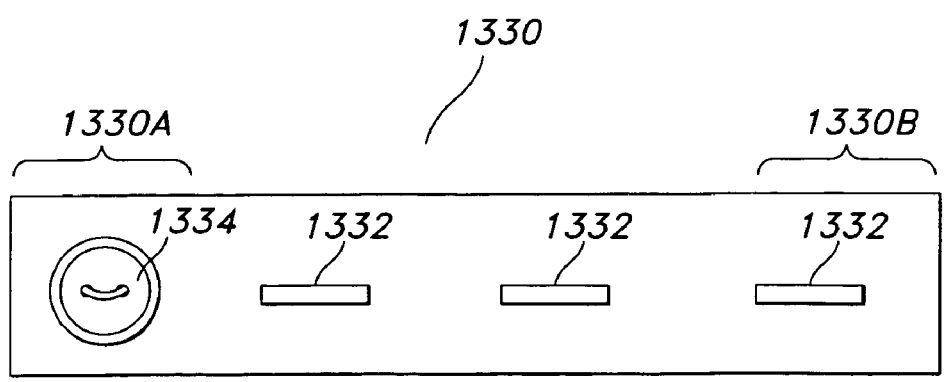
FIG. 17 is a front view of an embodiment of a belt extender configured for use with the undergarment illustrated in FIG. 16.

Referring now to FIGS. 15 through 17, exemplary undergarments according to yet another aspect of this invention will be described. The embodiments illustrated in FIGS. 15 through 17 are adapted to receive an absorbent pad, and the undergarment is 10 held in place on the user's body by a belt that is held in place by buttons. Details of the embodiments illustrated in FIGS. 15 through 17 are provided in U.S. Application No. 60/307,382, filed Jul. 25, 2001, entitled BELTED UNDERGARMENT WITH STATIONARY BUTTONED BELT AND CUFF.

FIG. 15 illustrates an undergarment 1210 having pad-receiving cuffs and a Is button attached belt. More specifically, the main body 1212 of the undergarment 1210 has two pad receiving cuffs 1214. These pad-receiving cuffs could be made with a resilient material at their edges 1216 to hold an absorbent pad (not shown) in place.

Located proximate the rear 1218 of the main body 1212 are a pair of belts 1220. The belts 1220 each terminate in an end that includes a button 1222. A belt 1224 that includes a plurality of buttonholes 1226 is provided. The plurality of buttonholes 1226 allows the user to adjust the diameter of the waist portion of the device undergarment 1210. Located at the front 1228 of the undergarment 1210 is another pair of buttonholes 1230 that cooperates with the above-mentioned terminal belt buttons 1222 and belted buttonholes 1226.

The belted undergarment 1210 is therefore configured to stay in place while the user can unbutton the front to check for dryness or to change the insert pad. Overlapping cuff features create a pocket for holding reusable or disposable pads.

Referring now to FIGS. 16 and 17, an exemplary embodiment of an undergarment 1310, and an embodiment of a belt extender 1330 configured for use with the undergarment 1310, are shown. The undergarment 1310 includes a rear portion 1316 and a pair of belts 1320 extending from the rear portion 1316. Each of the belts 1320 has a button 1322 at its end portion, and those buttons 1322 engage buttonholes provided in a stationary button strap 1350. The buttons 1322 at the ends of the belts 1320 also engage buttonholes 1324 provided in the front portion 1318 of the undergarment 1310. A pad-receiving cuff 1314 has an edge 1315. Pads (whether reusable or disposable) can be inserted into the cuffs.

By virtue of the stationary button strap 1350, a waist portion of the undergarment 1310 can be formed by engaging the belts 1320 to the buttoned belt 1350. The user can then complete the assembly of the undergarment 1310 by fastening the front portion 1318 of the undergarment 1310 to the stationary buttoned strap 1350 by means of buttons 1322 and buttonholes 1324 in the front portion 1318 of the garment.

Referring specifically to FIG. 17, a belt extender 1330 is optionally used in connection with the undergarment 1310 in order to extend one or more of the belts 1320, thereby providing a waist portion sized to fit larger individuals. More specifically, one of the buttonholes 1332 of the belt extender 1330 can be used to engage the belt extender 1330 to a belt 1320, and the extender button 1334 of the belt extender 1330 can then be used to bring about engagement between the belt extender 1330 and the stationary buttoned strap 1350. The belt extender 1330 can be used on one or both of the belts 1320 of the undergarment 1310, or not at all, depending on the needs of the individual wearer.

The configuration of the belt extender 1330 illustrated in FIG. 17 is optionally used for one or both of the belts 1320 of the undergarment 1310, thereby affording improved adjustability as described previously with respect to the embodiment illustrated in FIGS. 3 and 4. Although belt 1330 is illustrated with a button 1334 at one end portion 1330A and a buttonhole 1332 at the opposite end portion 1330B, buttons or buttonholes (or other engagement mechanisms) can be provided at both end portions 1330A and 1330B of the belt 1330.

The engaging means used in undergarments according to this invention may be any fastener conventionally used in the fastening art for garment applications, including but not limited to adhesives, hooks, buttons, or snaps and the like. For example, they may each include a surface carrying hooks and a surface engageable by hooks. Such surfaces include, but are not limited to, woven and non-woven materials comprising polypropylene, polyethylene, polyester, NYLON, or RAYON. Optionally, the hooks may be engageable by loops. Such products are for example available from the Velcro Corporation under the mark VELCRO.

Also optionally, the engaging means may comprise a double-sided fastener wherein there are opposite surfaces, one of which has hooks and the other of which has loops or other material capable of engaging hooks. Incorporating such a feature in two or more locations designed to be attached to each other may allow the user to lay the fastener parts down in a variable sequence, accommodating individual preferences, e.g., for left- or right-handed users.

Additionally, a double-sided fastener may further be constructed such that hooks are positioned in a region to define a border between an edge portion of the fastening means and the hooks, the border being completely or substantially devoid of hooks and the border substantially surrounding said region. Fastening tabs of this type are disclosed in a co-pending PCT patent application, filed Jul. 15, 2002, and titled DISPOSABLE AND REUSABLE PROTECTIVE UNDERGARMENTS, which is incorporated herein by reference.

Although the invention is illustrated and described herein with reference to specific embodiments, the invention is not intended to be limited to the details shown. Rather, various modifications may be made in the details within the scope and range of equivalents of the claims and without departing from the invention. In the figures and description herein, it is to be understood that the embodiments are exemplary but not limiting. In this spirit, for example, it should be noted that buttons, although shown in the figures as circular in shape, may in any and all of the embodiments of this invention be of any shape including but not limited to oval, square, triangular, spherical, and domed, for example, or any of these shapes in combination. Similarly, although the figures show buttonholes as being oriented horizontally on the devices of this invention as worn, they may also in all embodiments be vertical or biased or curved or otherwise oriented, or any of these orientations in combination.

Further, it is to be understood that any of the belts, belt extenders, and stationary straps shown or described may be constructed of a non-stretching material, or may comprise materials that render them stretchably resilient. Materials of both types are well known in the fabric and apparel art, and include for example the generic class of material commonly referred to as "elastic". Suitable materials might also include stretchable elements made from a natural or synthetic rubber or a spring.

Additionally, although certain embodiments disclosed herein are configured for reusable applications, the features of those embodiments apply equally to disposable products. Likewise, although certain embodiments disclosed herein are configured for disposable applications, the features of those embodiments apply equally to reusable products.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention. Having described the invention, we now claim the following and their equivalents.

What is claimed is:

1. An adjustable absorbent article comprising:
   an absorbent body configured to be positioned adjacent a wearer of said absorbent article; and
   at least one adjustable belt configured to be releasably attached to said absorbent body and to retain said absorbent body adjacent a wearer of said absorbent article, at least one end of said at least one belt having a button for engagement with a buttonhole on said absorbent body, said at least one belt having at least one buttonhole spaced from said button of said belt for engagement with said button of said belt to adjust the size of said belt.

2. The adjustable absorbent article of claim 1, wherein said absorbent body is disposable.

3. The adjustable absorbent article of claim 1, wherein said absorbent body is reusable.

4. The adjustable absorbent article of claim 1, wherein said absorbent body comprises at least two buttonholes and said at least one belt comprises a button at each of said ends, each of said buttons being positioned for engagement in one of said buttonholes.

5. The adjustable absorbent article of claim 1, said at least one belt comprising a plurality of buttonholes between said ends of said belt.

6. The adjustable absorbent article of claim 5, wherein a distance between adjacent buttonholes is substantially equal.

7. The adjustable absorbent article of claim 1, said at least one belt further comprising indicia to assist the wearer in sizing said adjustable absorbent article.

8. The adjustable absorbent article of claim 7, said indicia being selected from the group consisting of numerals, colors, shades, textures, and dimensions.

9. The adjustable absorbent article of claim 1, further comprising a belt extender having ends configured to be attached to said absorbent body and to said at least one belt respectively, one end of said belt extender having a buttonhole for engagement with said button on said belt, and an opposite end of said belt extender having a button for engagement with said buttonhole on said absorbent body.

10. The adjustable absorbent article of claim 1, wherein said at least one belt comprises a pair of belts each having ends configured to be attached to said body and to retain said body adjacent a wearer of said absorbent article.

11. The adjustable absorbent article of claim 1, said at least one belt comprising a resilient material.

12. The adjustable absorbent article of claim 1, said absorbent body having plural buttonholes and said adjustable absorbent article having plural belts, each of said belts having a button for engagement with a buttonhole on said absorbent body, and each of said belts having plural buttonholes between said buttons of said belt.

13. An adjustable absorbent article comprising:
    an absorbent body configured to be positioned adjacent a wearer of said absorbent article and having a plurality of buttonholes; and
    adjustable belts configured to be releasably attached to said absorbent body and to retain said absorbent body adjacent a wearer of said absorbent article, at least one end of each of said belts having a button for engagement with one of said buttonholes on said absorbent body, each of said belts having a plurality of buttonholes spaced from said buttons of said belts for optional selective engagement with said button of said belt to adjust the size of each of said belts.

14. An adjustable absorbent article comprising:
    an absorbent body configured to be positioned adjacent a wearer of said absorbent article; and
    an adjustable belt releasably attached to said body to help retain said absorbent body adjacent a wearer of said absorbent article, said belt having at least one button and at least one buttonhole, said buttonhole being positionable for engagement with said button of said belt, thereby reducing the size of said belt.

15. The adjustable absorbent article of claim 14, said belt comprising a plurality of buttons configured for engagement in said at least one buttonhole.

16. The adjustable absorbent article of claim 15, said belt comprising a plurality of buttonholes between a pair of said buttons.

17. The adjustable absorbent article of claim 14, said belt comprising a plurality of buttonholes configured for optional selective engagement with said at least one button of said belt.

18. The adjustable absorbent article of claim 14, said belt comprising a plurality of buttonholes and a plurality of buttons configured for engagement by one or more of said buttonholes of said belt.

19. The adjustable absorbent article of claim 14, said belt comprising a resilient material.

20. A belt configured for releasable attachment to an absorbent body of an absorbent article to retain the body adjacent a wearer of said absorbent article and for adjusting the size of the absorbent article, ends of said belt each having a button for engagement with a respective buttonhole on the absorbent body of the absorbent article, said belt having at least one buttonhole spaced from said buttons for engagement with one of said buttons of said belt to adjust the size of the belt.

21. An adjustable absorbent article comprising:
    an absorbent body configured to be positioned adjacent a wearer of said absorbent article;
    at least one belt having ends configured to be releasably engaged to said absorbent body;
    first means positioned on at least one of said ends of said belt for releasable engagement to said absorbent body; and
    second means positioned on said belt at a location spaced from said first means for releasable engagement to said first means to adjust the length of said belt.

22. The adjustable absorbent article of claim 21 comprising two or more belts each having ends, first means positioned on at least one of said ends of each of said belts for releasable engagement to said absorbent body, and second means positioned at a location spaced from said first means of each of said belts for releasable engagement to said first means to adjust the length of said belts.

23. The adjustable absorbent article of claim 22, first releasable engagement means being positioned on each of said ends of each of said belts for releasable engagement to said absorbent body.

24. The adjustable absorbent article of claim 21, wherein said first releasable engagement means is selected from the group consisting of a button, a buttonhole, a surface comprising hooks, a surface configured to engage hooks, and an adhesive.

25. The adjustable absorbent article of claim 21, wherein said second releasable engagement means is selected from the group consisting of a button, a buttonhole, a surface comprising hooks, a surface configured to engage hooks, and an adhesive.

26. The adjustable absorbent article of claim 21, wherein said first and second releasable engagement means are engageable to one another.

27. The adjustable absorbent article of claim 21, wherein said second releasable engagement means is positioned at plural locations spaced from said first releasable engagement means.

28. An adjustable absorbent article comprising:
   an absorbent body configured to be positioned adjacent a wearer of said absorbent article; and
   at least one belt configured to be releasably attached to said absorbent body and to help retain said absorbent body adjacent a wearer of said absorbent article, at least one end of said at least one belt having a button sewn to said at least one belt and positioned for engagement with a slotted buttonhole defined on said absorbent body, said at least one belt further having at least one slotted buttonhole defined on said at least one belt at a location spaced from said button of said belt for engagement with said button of said belt to adjust the size of said belt.

29. An adjustable absorbent article comprising:
   an absorbent body configured to be positioned adjacent a wearer of said absorbent article; and
   at least one belt configured to be releasably attached to said absorbent body and to help retain said absorbent body adjacent a wearer of said absorbent article, said at least one belt having a button positioned at said end and at least one buttonhole spaced from said button of said belt, thereby defining an intermediate belt between said button and said at least one buttonhole, wherein said at least one buttonhole is positioned for engagement with said button to retain said intermediate belt in a folded configuration to adjust the size of said belt.

30. An adjustable absorbent article comprising:
   an absorbent body configured to be positioned adjacent a wearer of said absorbent article, said absorbent body having plural buttonholes; and
   two adjustable belts each configured to be releasably attached to said absorbent body and to retain said absorbent body adjacent a wearer of said absorbent article, each end of each belt having a button for engagement with one of said plural buttonholes of said absorbent body, and each of said belts having plural buttonholes positioned between said buttons of said belt for engagement with a button of said belt to adjust the size of said belt.

* * * * *